(12) United States Patent
Galland et al.

(10) Patent No.: US 6,590,100 B2
(45) Date of Patent: Jul. 8, 2003

(54) PROCESS FOR PREPARING A POLYAROMATIC COMPOUND

(75) Inventors: Jean-Christophe Galland, Lyons (FR); Monique Savignac, Gif sur Yvette (FR); Jean-Pierre Genet, Verrieres le Buisson (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 10/146,263

(22) Filed: May 15, 2002

(65) Prior Publication Data

US 2002/0173652 A1 Nov. 21, 2002

Related U.S. Application Data

(63) Continuation of application No. 09/520,534, filed on Mar. 8, 2000, now abandoned.

(51) Int. Cl.$^7$ .............................. C07F 5/02; C07F 9/06; C07F 9/02; C07C 309/00
(52) U.S. Cl. .............................. 546/13; 546/6; 546/22; 546/304; 562/35; 562/41; 568/2; 568/16
(58) Field of Search ............................... 546/13, 6, 22, 546/304; 562/35, 41; 568/2, 16

(56) References Cited

PUBLICATIONS

Kaoru Inada et al Tetrahedron vol. 56 2000, pp. 8657–8660.*
Adriano Indolese, Tetrahedron Letters vol. 38, No. 20, pp. 3513–3516, 1997.*
Masato Ueda et al, tetrahedron 54 pp. 13079–13086, 1998.*
Syun Saito et al J. Organic Chemistry, 62, pp. 8024–8030, 1997.*
Tetrahedron Letters 40 (1999) 2323–2326.
Journal of Organic Chemistry 1995, Virgil Percec et al., Aryl Mesylates in Metal Catalyzed . . . vol. 60, pp. 1060–1065.
Tetrahedron, Dec. 1999, Bruce Lipshutz et al. Biaryls via Suzuki Cross–Coupling . . . Volu.56 (2000) 2139–2144.

* cited by examiner

Primary Examiner—D. Margaret Seaman

(57) ABSTRACT

The present invention provides a process for preparing a polyaromatic compound comprising at least one sequence of two aromatic rings.

The process of the invention, which consists in reacting an aromatic compound bearing a leaving group and an arylboronic acid and/or its derivatives in the presence of a base and an effective amount of a nickel catalyst, is characterized in that the reaction is conducted in a reaction solvent which is water optionally in a mixture with an organic solvent and in the presence of an effective amount of a catalyst based on nickel with at least one water-soluble phosphine ligand.

39 Claims, No Drawings

PROCESS FOR PREPARING A POLYAROMATIC COMPOUND

This application is a continuation of U.S. application Ser. No. 09/520,534, filed on Mar. 8, 2000 now abandoned.

The present invention relates to a process for preparing a polyaromatic compound.

The invention relates in particular to a compound of the biphenyl type.

In the subsequent specification of the present invention, the term "polycyclic aromatic compound" denotes a compound comprising at least one sequence of two aromatic, carbocyclic and/or heterocyclic rings.

The term "aromatic compound" denotes the classical concept of aromaticity as defined in the literature, in particular by Jerry MARCH, Advanced Organic Chemistry, 4th edition, John Wiley and Sons, 1992, pp. 40 et seq.

More simply, the expression "aryl" will be used to denote all aromatic compounds, whether carbocyclic aromatic compounds or heterocyclic aromatic compounds.

Structures of the biaryl type are encountered in numerous molecules which are used in the agrochemical sector, especially in herbicides or pesticides, or in the pharmaceutical sector. In particular, a process is sought for preparing compounds of the alkylbiphenyl or cyanobiphenyl type.

Miyaura Norio [Tetrahedron Letters 37, (17), pp. 2993–6 (1996)] describes the preparation of compounds of the biphenyl type in accordance with the Suzuki reaction, which involves reacting an arylboronic acid and a chlotoaromatic compound in the presence of a nickel catalyst, $NiCl_2$ (dppf), potassium phosphate, and butyllithium in dioxane.

The said process makes it possible to employ a choloroaromatic compound, which is of greater interest from an economic standpoint than a reactant of bromoaromatic type; however, the process has the disadvantage of being conducted in an organic solvent.

The object of the present invention is to provide a process for preparing compounds of the biaryl type in an aqueous or aqueous-organic medium.

What has now been found, and constitutes the subject-matter of the present invention, is a process for preparing a polycyclic aromatic compound comprising at least one sequence of two aromatic rings, which consists in reacting an aromatic compound bearing a leaving group and an arylboronic acid and/or its derivatives in the presence of a base and an effective amount of a nickel catalyst, characterized in that the reaction is conducted in a reaction solvent which is water optionally in a mixture with an organic solvent and in the presence of an effective amount of a catalyst based on nickel with at least one water-soluble phosphine ligand.

In accordance with the process of the invention, it has been found that it is possible to carry out a coupling reaction of an arylboronic acid and a haloaromatic compound in the presence of water if use is made of a catalyst based on nickel with a water-soluble phosphine ligand.

It is important according to the invention that the phosphine is water-soluble.

A first embodiment of the invention consists in preparing a complex of the nickel with the water-soluble phosphine in situ, by employing separately in the reaction medium a nickel salt or a complex of nickel and a water-soluble phosphine.

Another variant embodiment of the process of the invention is to prepare this type of complex beforehand, at the time of use, and then to introduce it into the reaction medium.

One advantage of the process of the invention lies in the use of a catalyst based on nickel which is less expensive than the palladium catalysts most frequently used in the coupling reactions of an arylboronic acid and a haloaromatic compound. Furthermore, nickel is a metal which is easily introduced into the C(aromatic)—Cl bond.

More precisely, the aromatic compound bearing at least one leaving group, referred to hereinafter as "haloaromatic compound" corresponds to the general formula (I):

in which:
- A symbolizes the radical of a ring which forms all or part of a carbocyclic or heterocyclic, aromatic, monocyclic or polycyclic system,
- R, which is identical or different at each occurrence, represents substituents on the ring,
- Y represents a leaving group, preferably a halogen atom or a sulphonic ester group of formula $—OSO_2—R$, in which R is a hydrocarbon group, and
- n represents the number of substituents in the ring.

In the formula of the sulphonic ester groups, R is a hydrocarbon group of arbitrary type. However, given that Y is a leaving group, it is of interest from an economic standpoint for R to be simple in nature, and to represent more particularly a linear or branched alkyl group having 1 to 4 carbon atoms, preferably a methyl or ethyl group, although it may also represent, for example, a phenyl or tolyl group or a trifluoromethyl group. Among the groups Y, the preferred group is a triflate group, which corresponds to a group R representing a trifluoromethyl group.

As preferred leaving groups it is preferred to select a bromine or chlorine atom.

The invention applies in particular to haloaromatic compounds corresponding to the formula (I) in which A is the radical of a cyclic compound having preferably at least 4 atoms in the ring, preferably 5 or 6, which is optionally substituted, and representing at least one of the following rings:
- a monocyclic or polycyclic aromatic carbocycle,
- a monocyclic or polycyclic aromatic heterocycle containing at least one of the heteroatoms O, N and S.

Without limiting the scope of the invention, it will be specified that the optionally substituted radical A represents the radical:

1.—of an aromatic, monocyclic or polycyclic carbocyclic compound.

The term "polycyclic carbocyclic compound" denotes:
- a compound consisting of at least two aromatic carbocycles which jointly form ortho-condensed or ortho- and peri-condensed systems;
- a compound consisting of at least two carbocycles only one of which is aromatic, which jointly form ortho-condensed or ortho- and peri-condensed systems.

2.—an aromatic, monocyclic or polycyclic heterocyclic compound.

The term "polycyclic heterocyclic compound" is defined as:
- a compound consisting of at least two heterocycles containing at least one heteroatom in each ring, at least one of the two rings being aromatic, and jointly forming ortho-condensed or ortho- and peri-condensed systems;

a compound consisting of at least one carbocycle and at least one heterocycle, at least one of the rings being aromatic, and jointly forming ortho-condensed or ortho- and peri-condensed systems.

More particularly, the optionally substituted radical A represents one of the following rings:

an aromatic carbocycle:

an aromatic bicycle comprising two aromatic carbocycles:

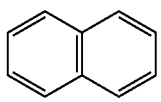

a partially aromatic bicycle containing two carbocycles one of which is aromatic:

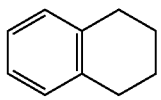

an aromatic heterocycle:

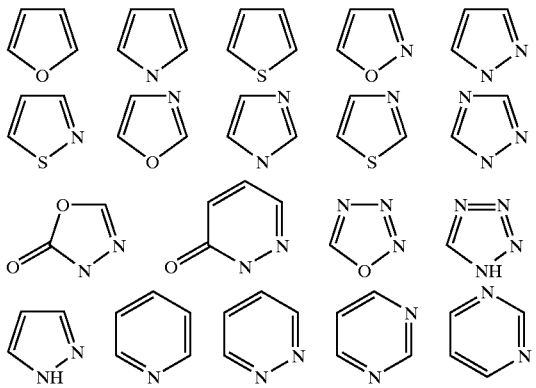

an aromatic bicycle comprising one aromatic carbocycle and one aromatic heterocycle:

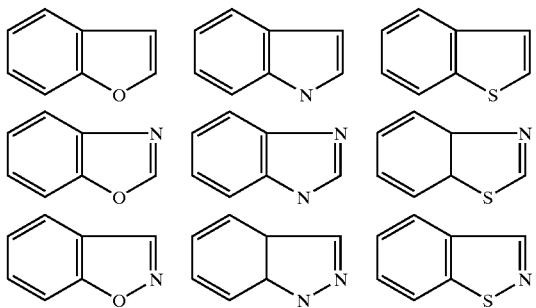

-continued

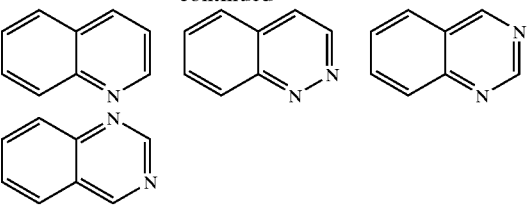

a partially aromatic bicycle comprising one aromatic carbocycle and one heterocycle:

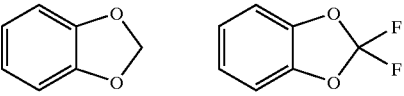

an aromatic bicycle comprising two aromatic heterocycles:

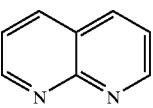

a partially aromatic bicycle comprising one carbocycle and one aromatic heterocycle:

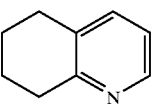

a tricycle comprising at least one carbocycle or one aromatic heterocycle:

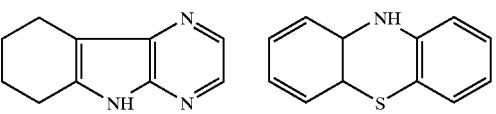

In the process of the invention, it is preferred to employ a haloaromatic compound of formula (I) in which A represents an aromatic nucleus, preferably a benzenic or naphthalenic nucleus.

The aromatic compound of formula (I) can bear one or two or more substituents.

The number of substituents present on the ring depends on the carbon condensation of the ring and on the presence or absence of unsaturations on the ring.

The maximum number of constituents which can be borne by a ring is readily determined by the person skilled in the art.

In the present text, the term "two or more" generally means less than 4 substituents on an aromatic nucleus.

Examples of substitutents are given hereinbelow, although this list is not limitative.

The identical or different group or groups R preferably represent one of the following groups:
  a linear or branched alkyl group having 1 to 6 carbon atoms, preferably 1 to 4 carbon atoms, such as methyl, ethyl, propyl, isopropyl, butyl, isobutyl, sec-butyl or tert-butyl,
  a linear or branched alkenyl or alkynyl group having 2 to 6 carbon atoms, preferably 2 to 4 carbon atoms, such as vinyl or allyl, a linear or branched thioether or alkoxy group having 1 to 6 carbon atoms, preferably 1 to 4 carbon atoms, such as the groups methoxy, ethoxy, propoxy, isopropoxy and butoxy, an alkenyloxy group, preferably an allyloxy group, or a phenoxy group, a cyclohexyl, phenyl or benzyl group, an acyl group having 2 to 6 carbon atoms, a group of formula:

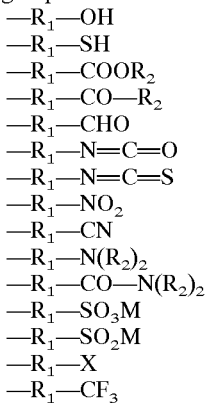

in which formulae $R_1$ represents a valency bond or a saturated or unsaturated linear or branched divalent hydrocarbon group having 1 to 6 carbon atoms, such as, for example, methylene, ethylene, propylene, isopropylene or isopropylidene; the groups $R_2$, which are identical or different, represent a hydrogen atom or a linear or branched alkyl group having from 1 to 6 carbon atoms or phenyl; M represents a hydrogen atom, an alkali metal, preferably sodium, or a group $R_2$; and X symbolizes a halogen atom, preferably a chlorine, bromine or fluorine atom.

The present invention applies especially to haloaromatic compounds corresponding to the formula (I) in which the group or groups R represent:

a linear or branched alkyl group having from 1 to 6 carbon atoms, preferably from 1 to 4 carbon atoms, such as methyl, ethyl, propyl, isopropyl, butyl, isobutyl, sec-butyl and tert-butyl, a linear or branched alkenyl group having 2 to 6 carbon atoms, preferably 2 to 4 carbon atoms, such as vinyl or allyl, a linear or branched alkoxy group having 1 to 6 carbon atoms, preferably 1 to 4 carbon atoms, such as the groups methoxy, ethoxy, propoxy, isopropoxy and butoxy, an alkenyloxy group, preferably an allyloxy group, or a phenoxy group, a group of formula:

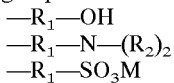

in which formulae $R_1$ represents a valency bond or a saturated or unsaturated linear or branched divalent hydrocarbon group having 1 to 6 carbon atoms, such as, for example, methylene, ethylene, propylene, isopropylene or isopropylidene; the groups $R_2$, which are identical or different, represent a hydrogen atom or a linear or branched alkyl group having 1 to 6 carbon atoms or phenyl; and M represents a hydrogen atom or a sodium atom.

In the formula (I), n is a number less than or equal to 4, preferably 0 or 1.

As examples of compounds which correspond to the formula (I) mention may be made in particular of 4-chloroacetophenone, 4-chlorobenzaldehyde, 4-chlorobenzophenone, 4-chlorotoluene, 1-chloro-4-trifluoromethylbenzene, 4-bromo-3-methylaniline, 1-amino-3-chloronaphthalene, 2-chloro-3-aminopyridine and 2-chlorobenzonitrile.

According to the invention, the haloaromatic compound of formula (I) reacts with arylboronic acid, which corresponds to the formula:

in which:

$R_3$ represents a monocyclic or polycyclic aromatic carbocyclic or heterocyclic group, $Q_1$ and $Q_2$, which are identical or different, represent a hydrogen atom, a linear or branched saturated or unsaturated aliphatic group having 1 to 20 carbon atoms, or a group $R_3$, or $Q_1$ and $Q_2$ can be connected to each other via an alkylene or alkylenedioxy group having 1 to 4 carbon atoms, or $Q_1$ and $Q_2$ can be connected to each other by —O—B—O— to form a boroxine group corresponding to the formula (III) in which $R_3$ has the meaning given above:

More specifically, the arylboronic acid corresponds to the formula (II) or (III) in which the group $R_3$ represents an aromatic carbocyclic or heterocyclic group. Consequently, $R_3$ can adopt the meanings given above for A. However, $R_3$ more particularly represents a carbocyclic group such as a phenyl or naphthyl group or a heterocyclic group such as a pyrrolyl, pyridyl, pyrimidinyl, pyridazinyl, pyrazolyl, pyrazinyl, 1,3-thiazolyl, 1,3,4-thiadiazolyl or thienyl group.

The aromatic ring can also be substituted. The number of substituents m is generally not more than 4 per ring, although m is usually 0 or 1. Reference may be made to the definition of R for examples of substituents.

The preferred substituents are alkyl or alkoxy groups having 1 to 4 carbon atoms, an amino group, a nitro group, a cyano group, a halogen atom, or a trifluoromethyl group.

As far as $Q_1$ and $Q_2$ are concerned, which are identical or different, they represent more particularly a hydrogen atom or a linear or branched acyclic aliphatic group having 1 to 20 carbon atoms which is saturated or includes one or more unsaturations on the chain, preferably 1 to 3 unsaturations, which are preferably simple or conjugated double bonds.

$Q_1$ and $Q_2$ preferably represent an alkyl group having 1 to 10 carbon atoms, preferably 1 to 4, or an alkenyl group having 2 to 10 carbon atoms, preferably a vinyl or 1-methylvinyl group.

$Q_1$ and $Q_2$ can adopt the meanings given for $R_3$, in particular, any ring may also bear a substituent as described above.

$R_3$ preferably represents a phenyl group.

It would not be departing from the scope of the present invention to employ derivatives of arylboronic acids, such as the anhydrides and the esters and, more particularly, the esters of alkyls having 1 to 4 carbon atoms.

As examples of arylboronic acids, mention may be made in particular of benzeneboronic acid, 2-thiopheneboronic acid, 3-thiopheneboronic acid, 4-methylbenzeneboronic acid, 3-methylthiophene-2-boronic acid, 3-aminobenzeneboronic acid, 3-aminobenzeneboronic hemisulphate acid, 3-fluorobenzeneboronic acid, 4-fluorobenzeneboronic acid, 2-formylbenzeneboronic acid, 3-formylbenzeneboronic acid, 4-formylbenzeneboronic acid, 2-methoxybenzeneboronic acid, 3-methoxybenzeneboronic acid, 4-methoxybenzeneboronic acid, 4-chlorobenzeneboronic acid, 5-chlorothiophene-2-boronic acid, benzo[b]furan-2-boronic acid, 4-carboxybenzeneboronic acid, 2,4,6-trimethylbenzeneboronic acid, 3-nitrobenzeneboronic acid, 4-(methylthio)benzeneboronic-acid, 1-naphthaleneboronic acid, 2-naphthaleneboronic acid, 2-methoxy-1-naphthaleneboronic acid, 3-chloro-4-fluorobenzeneboronic acid, 3-acetamidobenzeneboronic acid, 3-trifluoromethylbenzeneboronic acid, 4-trifluoromethylbenzeneboronic acid, 2,4-dichlorobenzeneboronic acid, 3,5-dichlorobenzeneboronic acid, 3,5-bis(trifluoromethyl)benzeneboronic acid, 4,4'-biphenyldiboronic acid, and the esters and anhydrides of such acids.

The amount of reactants employed is such that the arylboronic acid/haloaromatic compound molar ratio is advantageously greater than or equal to 1 and varies preferably between 1 and 1.2.

The process of the invention uses a nickel catalyst, which can also be in the form of a complex.

The nickel is present in oxidation state 0. It can be in a higher oxidation state if it is in combination with a reducing metal such as, for example, zinc, manganese and/or magnesium.

It is also possible to use Raney nickel as reducing agent.

Where the nickel is employed in a catalytic amount, i.e. an amount less than the stoichiometric amount, it is important to regenerate it in the course of the reaction by combining it likewise with a reducing metal.

As specific examples of nickel derivatives, mention may be made of nickel (II) halides, such as nickel (II) chloride, bromide or iodide; nickel (II) sulphate; nickel (II) carbonate; the salts of organic acids containing 1 to 18 carbon atoms, such as, in particular, acetate, propionate; nickel (II) complexes such as nickel (II) acetylacetonate, dichlorobis (triphenylphosphine)nickel (II), dibromobis(bipyridine) nickel (II); nickel (0) complexes such as bis(cycloocta-1,5-diene)nickel (0), bisdiphenylphosphinoethanenickel (0).

The nickel can be deposited on a support.

The support is selected such that it is inert under the conditions of the reaction.

Examples of supports which can be employed are mineral or organic supports, such as, in particular, carbon, activated carbon, acetylene black, silica, alumina, clays and, more particularly, montmorillonite, or equivalent materials, or else a polymeric resin, for example a polystyrene.

In general, the metal is deposited in an amount of from 0.5% to 95%, preferably from 1% to 5% of the weight of the catalyst.

The catalyst can be employed in the form of a powder, pellets or granules.

In accordance with the process of the invention, a salt or a complex of nickel is combined with a ligand or coordinating agent which is a water-soluble phosphine.

As mentioned above, this complex is generally produced in situ between the nickel derivative and the phosphine which is present. Alternatively, the said complex can be prepared at the time of use and introduced into the reaction medium. It is then possible to add, or not, an additional amount of free phosphine.

In a phosphine, the phosphorus atom is connected to three hydrocarbon groups having 1 to 20 carbon atoms, which can be of any type; for example, a linear or branched, saturated or unsaturated acyclic aliphatic group; a monocyclic or polycyclic saturated, unsaturated or aromatic heterocyclic or carbocyclic group; or a linear or branched saturated or unsaturated aliphatic group bearing a cyclic substituent.

Also, two phosphorus atoms can be connected to one another by a valency bond or a saturated or unsaturated linear or branched divalent hydrocarbon group having 1 to 6 carbon atoms.

In the water-soluble phosphine which is employed in the process according to the invention, at least one of the three hydrocarbon groups attached to the phosphorus bears a solubilizing group S which can be one or more hydroxyl groups and/or functional groups of anionic type, in particular $SO_2W$, $SO_3W$ or $COOW$ in which W represents a hydrogen atom or an alkali metal, preferably sodium, a phosphonate group or an ammonium group $N^+R_3$ or phosphonium group $P^+R_3$ in which groups R usually represent an alkyl group having 1 to 4 carbon atoms or a benzyl group.

Mention may be made in particular of phosphines of the triarylphosphine type, and more preferably of the triphenylphosphine type, whose solubility is provided by the presence on the aromatic rings of one or more hydroxyl groups and/or functional groups of anionic type, in particular $SO_3W$ or $COOW$ in which W represents a hydrogen atom or an alkali metal, preferably sodium. The said groups can be present on the aromatic ring or rings but can also be borne by a chain, preferably an alkyl chain having 1 to 4 carbon atoms.

Another type of water-soluble phosphine is that in which at least one of the hydrocarbon groups is an aromatic ring which bears at least one oxyalkylated group having 2 or 3 carbon atoms, preferably corresponding to the formula:

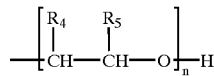

in which radicals $R_4$ and $R_5$, which are identical or different, represent a hydrogen atom or a methyl or ethyl radical; when one of the radicals $R_4$ and $R_5$ is a methyl or ethyl radical, the other radical $R_4$ or $R_5$, is then a hydrogen atom, n is a number between 1 and 50.

The radical $R_5$ preferably represents a hydrogen atom or a methyl radical. The radical $R_4$ preferably represents a hydrogen atom.

The number of oxyalkylenated units can vary widely between 1 and 50 but is preferably between 1 and 20.

It is also possible for the rings to include both oxyethylenated and oxypropylenated units, the said units being distributed at random or in blocks.

It is advantageous to employ aliphatic, cycloaliphatic, arylaliphatic or aromatic phosphines or mixed, aliphatic and/or cycloaliphatic and/or arylaliphatic and/or aromatic phosphines, and more particularly phosphines which correspond to the general formula (IV):

(IV)

in which:
the groups $R_6$, $R_8$, $R_9$ and $R_{10}$ which are identical or different, represent:
an alkyl radical having 1 to 12 carbon atoms,
a cycloalkyl radical having 5 or 6 carbon atoms,
a cycloalkyl radical having 5 or 6 carbon atoms which is substituted by one or more alkyl radicals having 1 to 4 carbon atoms or alkoxy radicals having 1 to 4 carbon atoms, a phenylalkyl radical whose aliphatic moiety contains 1 to 6 carbon atoms, a phenyl radical, a phenyl radical which is substituted by one or more alkyl radicals having 1 to 4 carbon atoms or alkoxy radicals having 1 to 4 carbon atoms, $R_7$ represents a valency bond or a saturated or unsaturated linear or branched divalent hydrocarbon group having 1 to 6 carbon atoms, q is 0 or 1, at least one of the groups $R_6$, $R_8$, $R_9$ and $R_{10}$ bears a solubilizing group S as defined.

Among the water-soluble phosphines of the formula (IV) it is preferred to employ a phosphine corresponding to the formula (IV) in which q is equal to 0 and $R_6$, $R_8$ and $R_9$ represent a phenyl group and one or three of the phenyl groups bear a solubilizing group of the $SO_3W$ type as defined above, or a diphosphine corresponding to the formula (IV) in which q is equal to 1, $R_7$ represents an ethylene group and $R_6$, $R_8$, $R_9$ and $R_{10}$ represent a phenyl group and one or four of the phenyl groups bear a solubilizing group of the $SO_3W$ type as defined above.

Examples of water-soluble phosphines include:

phosphines with sulphonated groups,

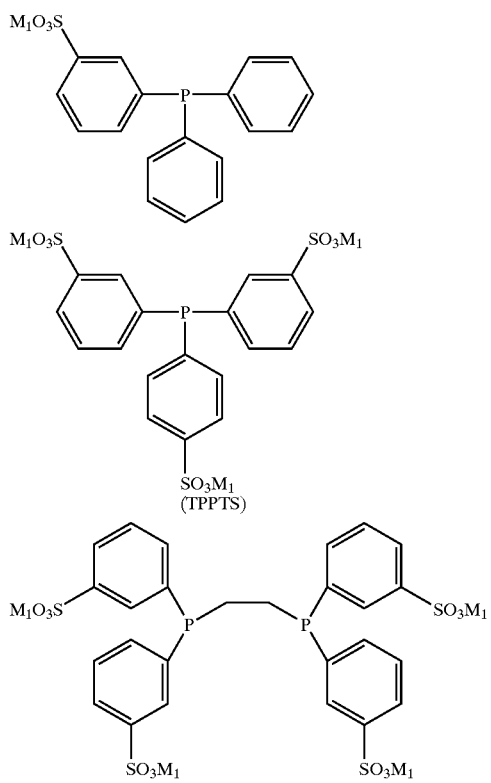

in which formulae $M_1$ represents a sodium atom or a group $NR_4$, R preferably representing an alkyl group having 1 to 4 carbon atoms, phosphines with quaternized aminoalkyl groups:

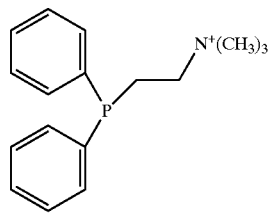

in which formula the counterion, which is not shown, is a halogen atom or a triflate or tetrafluoroborate ion, phosphines with carboxylic groups:

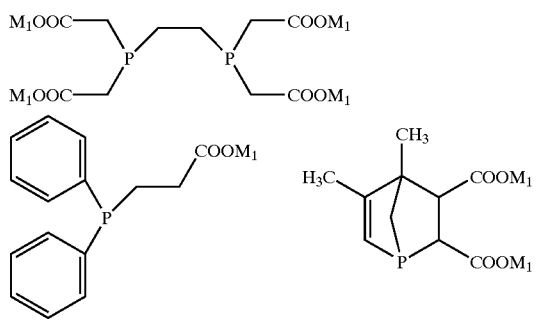

Among all of the phosphines defined above, it is advantageous to select TPPTS.

Reference may be made to the literature for the employment of water-soluble phosphines, in particular to FR-A 2743011 and FR-A 2739378.

As far as the proportions of catalyst, ligand and, if present, reducing metal are concerned, it is specified by way of indication that the amount of nickel catalyst, expressed by the molar ratio between the nickel (expressed in terms of the elemental metal) and the arylboronic acid varies between $5 \times 10^{-6}$ and 0.20, preferably between $6 \times 10^{-6}$ and 0.05.

The amount of water-soluble phosphine employed, expressed by the molar ratio between the water-soluble phosphine and the nickel, varies between 3 and 10, preferably between 3 and 5.

The amount of reducing metal employed represents the stoichiometric amount required to reduce $Ni^{++}$ to $Ni_0$ up to an excess representing from 100% to 500% of the stoichiometric amount.

In accordance with the process of the invention, the compounds (I) and (II) are reacted in the presence of a base.

As bases, use is made of alkali metal hydroxides or alkaline earth metal hydroxides, alkali metal carbonates or hydrogencarbonates, preferably barium hydroxide or caesium hydroxide, sodium carbonate or potassium carbonate, sodium hydrogencarbonate or potassium hydrogencarbonate, or metal phosphates, preferably sodium phosphate or potassium phosphate.

The amount of base employed, expressed by the ratio between the number of moles of $OH^-$ and the number of moles of arylboronic acid, is selected preferably between 2 and 4 and more preferably at approximately 2.0.

In accordance with the invention, the coupling of the haloaromatic compound and the arylboronic acid is conducted advantageously in water with or without the addition of an organic solvent.

The water is introduced into the reaction medium generally by way of the base.

The amount of water added is such that the medium is stirrable. It represents advantageously from 50 to 100% of the volume of water+organic solvent.

The starting reactant, namely the haloaromatic compound, can be used as the reaction solvent, but it is also possible to employ an organic solvent.

An organic solvent is selected which is less activated than the starting substrate and which preferably solubilizes it.

As examples of solvents suitable for the present invention, mention may be made in particular of aliphatic, cycloaliphatic or aromatic ethers, ketones and amides.

By way of example of ethers, mention may be made more particularly of dipropyl ether, diisopropyl ether, dibutyl ether, methyl tert-butyl ether, ethylene glycol dimethyl ether (or glyme), diethylene glycol dimethyl ether (or diglyme); phenyl ether; dioxane and tetrahydrofuran (THF).

As far as the ketones are concerned, mention may be made more particularly of acetone, methyl isobutyl ketone, cyclopentanone and cyclohexanone.

As examples of solvents of amide type mention may be made more specifically of dimethylformamide, diethylacetamide and N-methylpyrrolidone.

Other solvents which can also be mentioned are dimethyl sulphoxide and sulpholane.

It is also possible to use a mixture of organic solvents.

As far as the concentration of the arylboronic acid in the reaction medium is concerned, it is preferably between 10% and 50% by weight and, more preferably, between 20% and 30%.

The reaction temperature is advantageously between the ambient temperature (which is usually between 15 and 25° C.) and 150° C. and, preferably, between 50 and 100° C.

Generally, the reaction is conducted under the autogenous pressure of the reactants.

In accordance with one preferred variant embodiment of the process according to the invention, the process of the invention is conducted under a controlled atmosphere of inert gases. It is also possible to establish an atmosphere of nobel gases, preferably argon, but it is more economical to employ nitrogen.

From a practical standpoint, the process is simple to implement. One preferred embodiment consists in charging the water, optionally the organic solvent and then the water-soluble phosphine, the reducing agent, and the nickel salt or complex. This charge is heated at between 60 and 100° C. for 1 to 3 hours in order to prepare the complex.

The haloaromatic compound and the boronic acid are optionally added in an organic solvent.

The mixture is heated to the reaction temperature.

The polycyclic aromatic compound is recovered in a conventional manner, for example by extraction with an organic solvent, and mention may be made in particular of ethers, preferably isopropyl ether; and halogenated or non-halogenated aliphatic or aromatic hydrocarbons, preferably toluene.

A polyaromatic compound is obtained which can be represented by the formula (V):

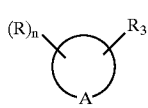

(V)

in which formula (V), A, R, $R_3$ and n have the meaning given above.

The process of the invention makes it possible to carry out the coupling of a haloaromatic compound and a boronic acid in the presence of water.

Exemplary embodiments of the invention are given hereinbelow.

In the examples, the abbreviations have the following meanings: TPPTS stands for sodium triphenylphosphinotrimetasulphonate.

The yield corresponds to the ratio between the number of moles of product formed and the number of moles of substrate (haloaromatic compound) deployed.

EXAMPLES

The procedure followed in the examples below is as follows:

Water and solvents were degassed before use and experiments are run under argon.

TPPTS (0.5 eq, 0.25 mmol, 473 mg of a 30% wt. solution in water), Zn (0.5 eq, 0.25 mmol, 16.4 mg) and $NiCl_2$(dppe) (10% mol, 0.05 mmol, 26.4 mg) were placed in a Schlenk tube under argon.

0.3 ml of water was added and the suspension was vigorously stirred at 80° C. for two hours.

The solution was cooled at 50° C. after which a solution of boronic acid (1.1 eq, 0.55 mmol) in 1 ml of 1,4-dioxane was added.

The chloroaromatic compound (1.0 eq, 0.5 mmol) and 0.4 ml (3.0 eq) of a 3.7 M aqueous $K_3PO_4$ solution were quickly introduced and the resulting mixture was stirred overnight (about 12 hours) at the temperature given hereafter in the examples, then quenched with 7 ml of saturated $NH_4Cl$ solution and extracted with 3×20 ml of ether.

The organic layer was washed with 20 ml of brine, dried over $MgSO_4$, filtered and concentrated in vacuo.

The crude product was purified by flash chromatography on silica gel to give the expected product.

Examples 1 to 5

In this series of examples, phenylboronic acid and different haloaromatic compounds, which are specified in Table (I) below, are reacted at different temperatures.

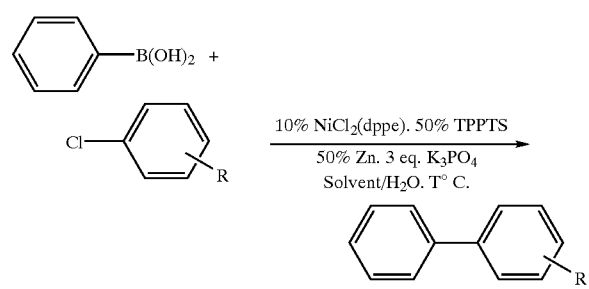

The tests are conducted in accordance with the procedure defined above and the results are set out in Table (I):

TABLE (I)

| Ref | R | Solvent | T(° C.) | Product | Yield* |
|---|---|---|---|---|---|
| 1 | 4-COCH₃ | 1,4-dioxane | 50 | Ph–C₆H₄–COCH₃ | (79%) |
| 2 | 4-CHO | 1,4-dioxane | 50 | Ph–C₆H₄–CHO | 81% (85%) |
| 3 | 4-COPh | 1,4-dioxane | 50 | Ph–C₆H₄–COPh | 70% |
| 4 | 4-CF₃ | DMF[b] | 80 | Ph–C₆H₄–CF₃ | 80% (85%) |
| 5 | 4-CH₃ | NMP | 80 | Ph–C₆H₄–CH₃ | 70% (76%) |

*Isolated yield GPC conversions are given inside brackets.

Examples 6 to 12

In this series of examples, 4-chloroacetophenone is reacted with different boronic acids, which are specified in Table (II) below.

The reaction takes place at 50° C.

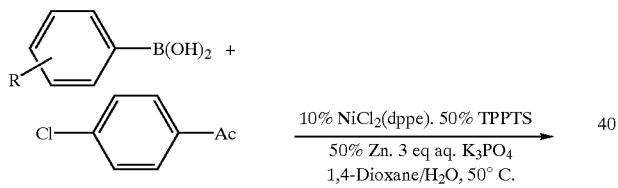

The tests are conducted in accordance with the procedure defined above and the results are set out Table (II):

TABLE (II)

| Ref. | ArB(OH)₂ | Product | Yield* |
|---|---|---|---|
| 6 | MeO–C₆H₄–B(OH)₂ | MeO–C₆H₄–C₆H₄–Ac | 81% |
| 7 | F–C₆H₄–B(OH)₂ | F–C₆H₄–C₆H₄–Ac | 86% |
| 8 | 3-H₂N–C₆H₄–B(OH)₂ | 3-H₂N–C₆H₄–C₆H₄–Ac | 47% |

TABLE (II)-continued

| Ref. | ArB(OH)₂ | Product | Yield* |
|---|---|---|---|
| 9 | | | 94% |
| 10[b] | | | 67% |
| 11 | | | 99% |
| 12 | | | 72% |

*Isolated yield.
[b]: 3-Methyl-4-chloroacetophenone was used.

Example 13

The procedure defined above is repeated, using 4-methylphenylboronic acid and 2-chlorobenzonitrile.

The reaction takes place at 80 °C.

The yield obtained is 70%.

What is claimed is:

1. A process for preparing a polycyclic aromatic compound comprising at least one sequence of two aromatic rings, comprising the steps of:
   a) Carrying out a reaction of an aromatic compound bearing a leaving group with an arylboronic acid or its derivatives in the presence of a base and an effective catalyzing amount of a nickel catalyst for said reaction, and
   b) carrying out the reaction of step a) in a reaction solvent which is water, optionally mixed with an organic solvent, said catalyst comprising nickel and at least one water-soluble phosphine ligand.

2. A process according to claim 1, wherein the aromatic compound bearing a leaving group corresponds to the general formula (I):

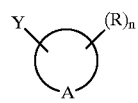

(I)

wherein:
   A is a ring which forms all or part of a carbocyclic or heterocyclic, aromatic, monocyclic or polycyclic system,
   R, which is identical or different at each occurrence, represents substituents on the ring,
   Y represents a leaving group, and
   n represents the number of substituents in the ring.

3. A process according to claim 2, wherein Y is a halogen atom or a sulphonic ester group of formula —OSO₂—R, wherein R is a hydrocarbon group.

4. A process according to claim 3, wherein the aromatic compound bearing a leaving group corresponds to the formula (I) wherein R is a linear or branched alkyl group having 1 to 4 carbon atoms.

5. A process according to claim 2, wherein R is methyl, ethyl, phenyl, tolyl, or trifluoromethyl.

6. A process according to claim 2, wherein A is the ring of a cyclic compound, optionally substituted, and representing at least one of the following rings:
   a monocyclic aromatic carbocycle,
   a polycyclic aromatic carbocycle,
   a monocyclic aromatic heterocycle comprising at least one of the heteroatoms O, N and S, or
   a polycyclic aromatic heterocycle comprising at least one of the heteroatoms O, N and S.

7. A process according to claim 2, wherein A represents a benzenic or naphthalenic nucleus.

8. A process according to claim 2, wherein the aromatic compound bearing a leaving group bears one or more substituents selected from the group consisting of a linear or branched alkyl group having 1 to 6 carbon atoms, a linear or branched alkenyl or alkynyl group having 2 to 6 carbon atoms, a linear or branched thioether, a linear or branched alkoxy group having 1 to 6 carbon atoms, an alkenyloxy group, a phenoxy group, a cyclohexyl, aphenyl, a benzyl group, an acyl group having 2 to 6 carbon atoms, a group of formula:

—R₁—OH,
—R₁—SH,

—R₁—COOR₂,
—R₁—CO—R₂,
—R₁—CHO,
—R₁—NO₂,
—R₁—CN,
—R₁—N(R₂)₂,
—R₁—CO—N(R₂)₂,
—R₁—SO₃M,
—R₁—SO₂M,
—R₁—X, or
—R₁—CF₃, wherein R₁ represents a valency bond or a saturated or unsaturated linear or branched divalent hydrocarbon group having 1 to 6 carbon atoms; R₂ radicals, which are identical or different, represent a hydrogen atom or a linear or branched alkyl group having from 1 to 6 carbon atoms or phenyl; M represents a hydrogen atom, an alkali metal, or a group R₂; and X is a halogen atom.

9. A process according to claim 8, wherein n is a number less than or equal to 4.

10. A process according to claim 2, wherein the aromatic compound bearing a leaving group is 4-chloroacetophenone, 4-chlorobenzaldehyde, 4-chlorobenzophenone, 4-chlorotoluene, 1-chloro-4-trifluoromethylbenzene, 4-bromo-3-methylaniline, 1-amino-3-chloro-naphthalene, 2-chloro-3-aminopyridine or 2-chlorobenzonitrile.

11. A process according to claim 1, wherein the arylboronic acid corresponds to the formula:

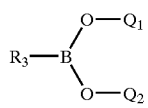

(II)

wherein:
R₃ represents a monocyclic or polycyclic aromatic carbocyclic or heterocyclic group,
Q₁ and Q₂, which are identical or different, represent a hydrogen atom, a linear or branched saturated or unsaturated aliphatic group having 1 to 20 carbon atoms, or a group R₃,
or Q₁ and Q₂ can be connected to each other via an alkylene or alkylenedioxy group having 1 to 4 carbon atoms,
or Q₁ and Q₂ can be connected to each other by —O—B—O— to form a boroxine group corresponding to the formula (III) wherein R₃ has the meaning given above:

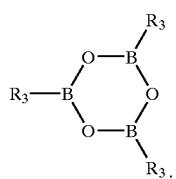

(III)

12. A process according to claim 11, wherein R₃ represents a phenyl, naphthyl, pyrrolyl, pyridyl, pyrimidinyl, pyridazinyl, pyrazolyl, pyrazinyl, 1,3-thiazolyl, 1,3,4-thiadiazolyl or thienyl group.

13. A process according to claim 11, wherein the arylboronic acid has an aromatic ring bearing one or more alkyl groups having from 1 to 4 carbon atoms, alkoxy groups having from 1 to 4 carbon atoms, amino groups, nitro groups, cyano groups, halogen atoms or trifluoromethyl groups.

14. A process according to claim 11, wherein Q₁ and Q₂, which are identical or different, represent a hydrogen atom, a linear or branched acyclic aliphatic group having 1 to 20 carbon atoms, optionally saturated with 1 to 3 unsaturations, or a group R₃.

15. A process according to claim 10, wherein the arylboronic acid is benzeneboronic acid, 2-thiopheneboronic acid, 3-thiopheneboronic acid, 4-methylbenzeneboronic acid, 3-methylthiophene-2-boronic acid, 3-aminobenzeneboronic acid, 3-aminobeazeneboronic hemisulphate acid, 3-fluorobenzeneboronic acid, 4-fluorobenzeneboronic acid, 2-formylbenzeneboronic acid, 3-formylbenzeneboronic acid, 4-formylbenzeneboronic acid, 2-methoxybenzeneboronic acid, 3-methoxybenzeneboronic acid, 4-methoxybenzeneboronic acid, 4-chlorobenzeneboronic acid, 5-chlorothiophene-2-boronic acid, benzo[b]furan-2-boronic acid, 4-carboxybenzeneboronic acid, 2,4,6-trimethylbenzeneboronic acid, 3-nitrobenzeneboronic acid, 4-(methylthio)benzeneboronic acid, 1-naphthaleneboronic acid, 2-naphthaleneboronic acid, 2-methoxy-1-naphthaleneboronic acid, 3-chloro-4-fluorobenzeneboronic acid, 3-acetamidobenzeneboronic acid, 3-trifluoromethylbenzeneboronic acid, 4-trifluoromethylbenzeneboronic acid, 2,4-dichlorobenzeneboronic acid, 3,5-dichlorobenzeneboronic acid, 3,5-bis(trifluoromethyl)benzeneboronic acid, 4,4'-biphenyldiboronic acid, the esters or the anhydrides of such acids.

16. A process according to claim 1, wherein the arylboronic acid/aromatic compound bearing a leaving group molar ratio is greater than or equal to 1.

17. A process according to claim 16, wherein the ratio is between 1 and 1.2.

18. A process according to claim 1, wherein the nickel catalyst comprises nickel in oxidation state 0 or higher in combination with a reducing metal.

19. A process according to claim 18, wherein the reducing metal is zinc, manganese, or magnesium.

20. A process according to claim 1, wherein the nickel catalyst is a nickel(II) halides; nickel(II) sulphate; nickel(II) carbonate; a salt of organic acids containing 1 to 18 carbon atoms; nickel(II) acetylacetonate, dichlorobis(triphenylphosphine)nickel(II); dibromobis(bipyridine)nickel(II); nickel(0); bis(cycloocta-1,5-diene)nickel(0); or bisdiphenylphosphinoethanenickel(0).

21. A process according to claim 20, wherein the nickel catalyst is nickel(II) chloride in combination with zinc.

22. A process according to claim 1, wherein the water-soluble phosphine carries on at least one of the three hydrocarbon groups attached to the phosphorus a solubilizing group S which is hydroxyl groups, anionic groups, an ammonium group, a phosphonium group or an oxyalkylated group having 2 or 3 carbon atoms, corresponding to the formula:

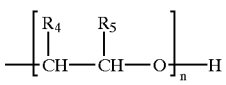

wherein the radicals R₄ and R₅ which are identical or different, represent a hydrogen atom or a methyl or ethyl radical; when one of the radicals R₄ or R₅ is a methyl or ethyl radical, the other radical $R_4$ or $R_5$ is then a hydrogen atom; and n is a number between 1 and 50.

23. A process according to claim 22, wherein the water-soluble phosphine comprises as anionic functional group, a group $SO_3W$ or $COOW$ wherein W represents a hydrogen atom or an alkali metal.

24. A process according to claim 23, wherein the water-soluble phosphine corresponds to the general formula (IV):

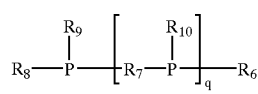
(IV)

wherein:
the groups $R_6$, $R_8$, $R_9$ and $R_{10}$ which are identical or different, represent:
an alkyl radical having 1 to 12 carbon atoms,
a cycloalkyl radical having 5 or 6 carbon atoms,
a cycloalkyl radical having 5 or 6 carbon atoms which is substituted by one or more alkyl radicals having 1 to 4 carbon atoms or alkoxy radicals having 1 to 4 carbon atoms,
a phenylalkyl radical whose aliphatic moiety contains 1 to 6 carbon atoms,
a phenyl radical, or
a phenyl radical which is substituted by one or more alkyl radicals having 1 to 4 carbon atoms or alkoxy radicals having 1 to 4 carbon atoms,
$R_7$ represents a valency bond or a saturated or unsaturated linear or branched divalent hydrocarbon group having 1 to 6 carbon atoms,
q is 0 or 1, and
at least one of the groups $R_6$, $R_8$, $R_9$ and $R_{10}$ bears a solubilizing group.

25. A process according to claim 24, wherein q is equal to 0 and $R_6$, $R_8$ and $R_9$ represent a phenyl group and one or three of the phenyl groups bear a solubilizing group of the formula $SO_3W$, wherein W represents a hydrogen atom or an alkali metal, or q is equal to 1, $R_7$ represents an ethylene group and $R_6$, $R_8$, $R_9$ and $R_{10}$ represent a phenyl group and one or four of the phenyl groups bear a solubilizing group of formula $SO_3W$.

26. A process according to claim 22, wherein the water-soluble phosphine is TPPTS.

27. A process according to claim 1, wherein the amount of nickel catalyst, expressed by the molar ratio between the nickel and the arylboronic acid, is between $5 \times 10^{-6}$ and 0.2.

28. A process according to claim 27, wherein the amount of nickel catalyst is between $5 \times 10^{-6}$ and 0.05.

29. A process according to claim 1, wherein the amount of water-soluble phosphine, expressed by the molar ratio between the said phosphine and the nickel, is between 3 and 10.

30. A process according to claim 1, wherein the amount of reducing metal represents a stoichiometric amount required to reduce $Ni^{++}$ to $Ni_0$ up to an excess representing from 100% to 500% of said stoichiometric amount.

31. A process according to claim 1, wherein the base is alkali metal hydroxides, alkaline earth metal hydroxides, alkali metal carbonates, alkali metal hydrogencarbonates, metal phosphates, or potassium phosphates.

32. A process according to claim 1, wherein the amount of base, expressed by the ratio between the number of moles of $OH^-$ and the number of moles of arylboronic acid, is between 2 and 4.

33. A process according to claim 1, wherein the water is present in an amount representing from 50 to 100% of the total weight of water and, optionally the organic solvent.

34. A process according to claim 1, wherein the organic solvent is aliphatic ethers; cycloaliphatic ethers; aromatic ethers; ketones; amides; dimethyl sulphoxide and sulpholane.

35. A process according to claim 1, wherein the catalyst is a complex of nickel with the water-soluble phosphine, optionally prepared in situ.

36. A process according to claim 1, wherein the reaction temperature is between ambient temperature and 150° C.

37. A process according to claim 1, wherein the reaction is conducted under an inert gas atmosphere.

38. A process according to claim 2, wherein the product obtained corresponds to the formula (V):

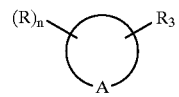
(V)

wherein, A, R, and n have the meaning given above, and $R_3$ represents a monocyclic or polycyclic aromatic carbocyclic or heterocyclic group.

39. A process according to claim 1, wherein the product obtained is 4-methylbiphenyl, 4-methoxybiphenyl, 4-trifluoro-methylbiphenyl or 2-p-tolylbenzonitrile.

* * * * *